(12) United States Patent
Buttry et al.

(10) Patent No.: US 7,205,100 B2
(45) Date of Patent: Apr. 17, 2007

(54) METHODS FOR REDUCING BACKGROUND FLUORESCENCE

(75) Inventors: Daniel Buttry, Laramie, WY (US);
Angie M. Oppedahl, Boone, IA (US);
Steven J. Lasky, Ankeny, IA (US);
Edward A. Orr, The Woodlands, TX (US)

(73) Assignee: Advanced Analytical Technologies, Inc., Ames, IA (US)

( * ) Notice: Subject to any disclaimer, the term of this patent is extended or adjusted under 35 U.S.C. 154(b) by 336 days.

(21) Appl. No.: 10/681,568

(22) Filed: Oct. 9, 2003

(65) Prior Publication Data

US 2004/0137524 A1 Jul. 15, 2004

Related U.S. Application Data

(60) Provisional application No. 60/417,168, filed on Oct. 10, 2002.

(51) Int. Cl.
*C12Q 1/00* (2006.01)
*C12Q 1/02* (2006.01)
*C12Q 1/68* (2006.01)
*G01N 1/30* (2006.01)
*G01N 33/53* (2006.01)

(52) U.S. Cl. .................. 435/4; 435/5; 435/6; 435/7.1; 435/7.2; 435/40.5; 435/962

(58) Field of Classification Search .................. 435/5, 435/4, 6, 7.1, 7.2, 40.5, 962
See application file for complete search history.

(56) References Cited

U.S. PATENT DOCUMENTS

| 5,436,134 | A |   | 7/1995 | Haugland et al. | 435/34 |
| 5,445,946 | A |   | 8/1995 | Roth et al. | 435/34 |
| 5,582,982 | A | * | 12/1996 | Cubbage et al. | 435/6 |
| 6,197,593 | B1 |  | 3/2001 | Deka et al. | 436/63 |
| 6,221,612 | B1 |  | 4/2001 | Knapp et al. | 435/7.1 |

OTHER PUBLICATIONS

Aldrich Handbook of Fine Chemicals and Laboratory Equipment. 2000-2001, pp. 28 and 121.*
Kano et al. Journal of Physical Chemistry, (1983), vol. 87, No. 4, pp. 566-569.*

* cited by examiner

*Primary Examiner*—Vera Afremova
(74) *Attorney, Agent, or Firm*—Fredrikson & Byron, P.A.

(57) ABSTRACT

This invention relates to methods for reducing background fluorescence in cell detection and measurement systems. In accordance with one aspect of the invention, cell-impermeant chemical agents are used to modify the fluorescent probes that reside outside the cells to be detected. The chemical agents can chemically modify one or more functional groups in the probes, thereby reducing or eliminating the fluorescence of the probes. In accordance with another aspect of the invention, Acid Black 48 is used to reduce background fluorescence produced by fluorescent probes such as SYTO 62.

11 Claims, 5 Drawing Sheets

US 7,205,100 B2

METHODS FOR REDUCING BACKGROUND FLUORESCENCE

This application claims benefit of 60/417,168 filed on Oct. 10, 2002.

1.0 TECHNICAL FIELD

This invention relates to methods for reducing background fluorescence in cell detection and measurement systems.

2.0 BACKGROUND

Fluorescent probes have been widely used in cell detection and measurement systems. Background fluorescence limits the ability of these systems to distinguish labeled cells from non-specific fluorescent signals. Background fluorescence can be generated when excess fluorescent probes exist outside the labeled cells. The excess probes can be freely dissolved in the test sample, producing a continuous, high level of background noise. They can also aggregate or bind to particulate materials in the test sample.

Unlike the freely dissolved probes, the fluorescent aggregates or particulates can be recognized as cells by detection instruments, leading to false positive signals. If there are large numbers of such particles, the fact that their fluorescent bursts occur very close together and at a high rate can overwhelm the data system of typical cell detection systems. Therefore, it is desirable to reduce background fluorescence produced by these aggregates and particulates.

U.S. Pat. No. 6,221,612 describes methods of using various dyes to reduce undesirable light emission. According to the disclosure, dyes which have absorption spectra that overlap with the absorption, emission or excitation spectrum of a fluorescent probe can be used to decrease background fluorescence generated by that probe. However, different dyes have different chemical and fluorescence properties. Selecting a suitable dye for a particular fluorescent probe and finding the proper conditions to use the dye may require extensive research.

3.0 SUMMARY OF THE INVENTION

In one embodiment, the present invention uses Acid Black 48 as an effective quencher for reducing background fluorescence produced by various fluorescent probes, such as the nucleic acid probe SYTO 62 (manufactured by Molecular Probes, Inc., Eugene, Oreg.). Alternatively or simultaneously, the chemical reagents reactive to the fluorophore in a fluorescent probe are used to effectively reduce background fluorescence produced by the fluorescent probe.

In accordance with one aspect of the invention, a method is provided for reducing background fluorescence. The method comprises the steps of (1) labeling cells of interest in a solution with a fluorescent agent, and (2) adding to the solution a chemical agent which is reactive to the fluorescent agent. The fluorescent agent is permeant to the cells, while the chemical agent is cell-impermeant. The chemical agent chemically modifies extracellular fluorescent agent in the solution such that the fluorescence emission produced by the solution, after subtracting the fluorescence emission produced by the labeled cells, is reduced by at least 10% after the chemical agent is added as compared to before the chemical agent is added.

In accordance with another aspect of this invention, another method is provided for reducing background fluorescence. The method comprises the steps of (1) labeling cells of interest with a fluorescent agent which is permeant to the cells, and (2) adding Acid Black 48 to the solution. The fluorescence emission produced from the solution, after subtracting the fluorescence emission produced from the labeled cells, is reduced by at least 10% after Acid Black 48 is added as compared to before Acid Black 48 is added. The labeled cells can be detected using a flow cytometer. Preferably, the fluorescent probe is SYTO 62.

4.0 BRIEF DESCRIPTION OF THE DRAWINGS

The following drawings are provided for illustration, not limitation:

Figure 4:
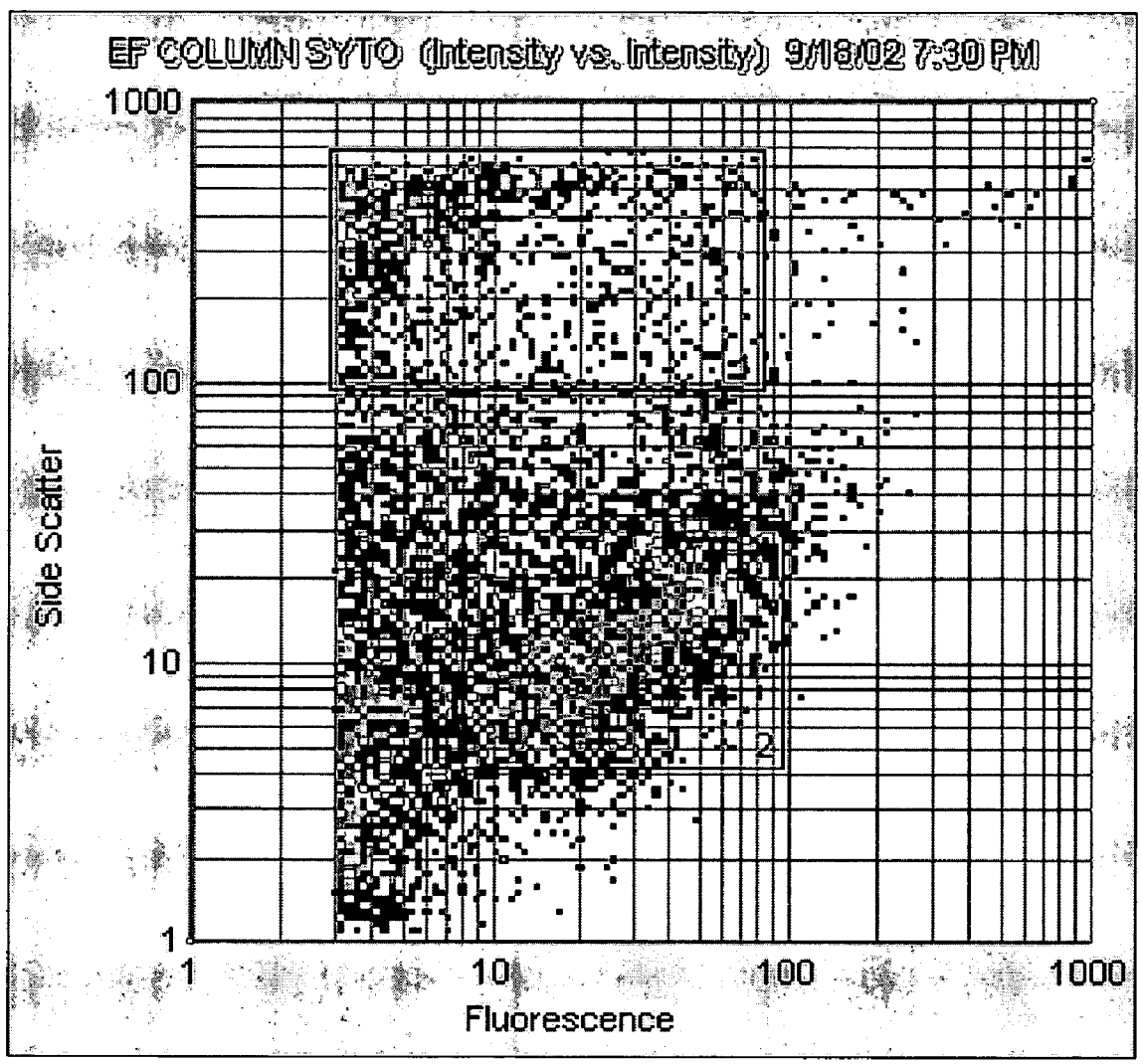
Figure 5:
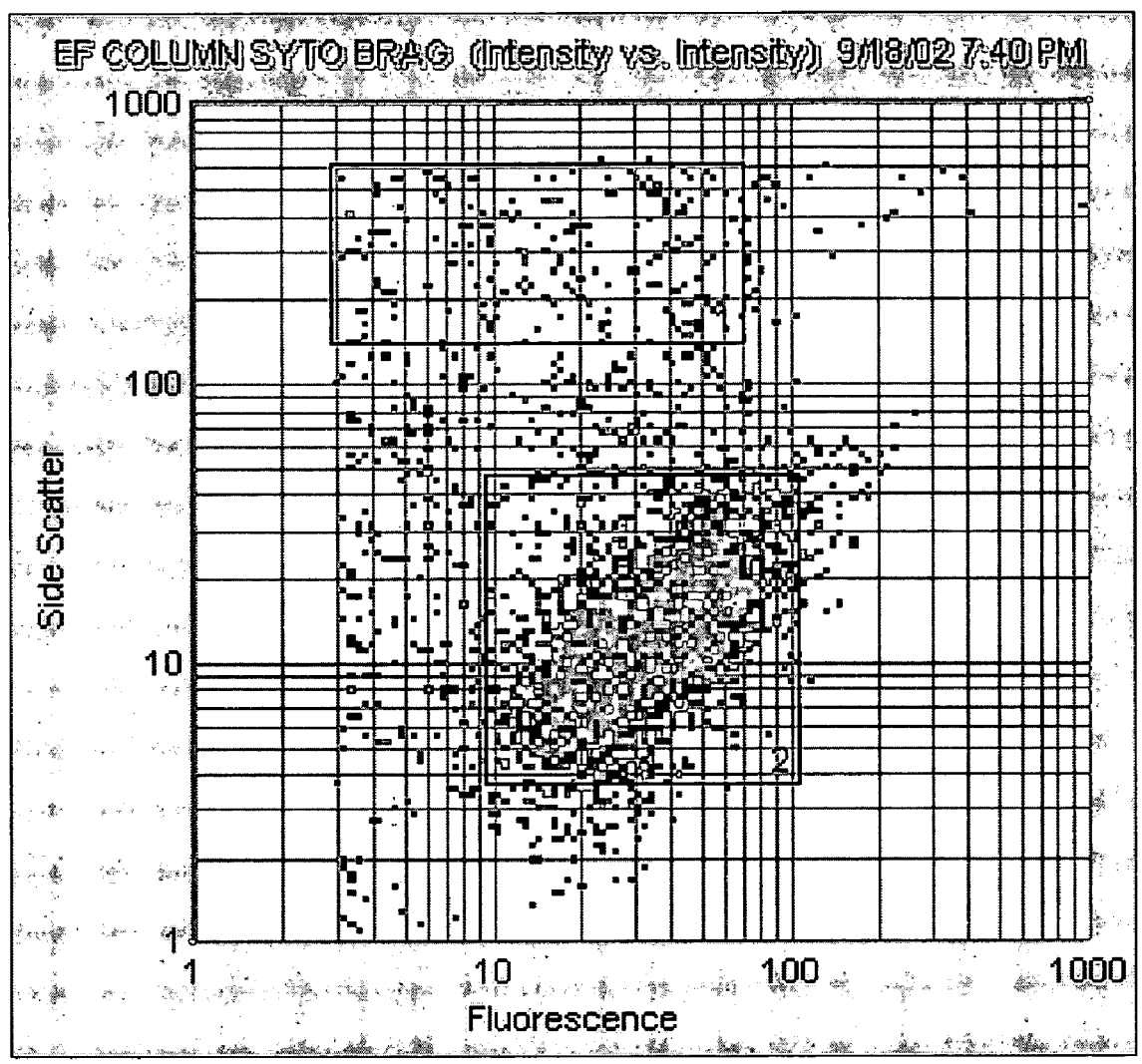

FIG. 4 demonstrates a side scatter versus fluorescence plot of a solution containing bacteria labeled with Syto 62; and FIG. 5 shows a side scatter versus fluorescence plot of a solution containing Syto 62-labeled bacteria and Acid Black 48.

5.0 DETAILED DESCRIPTION

In accordance with one aspect of the invention, chemical agents are used to reduce or eliminate background fluorescence. The chemical agents can chemically modify the fluorescent probes that reside outside the cells to be detected. Preferably, the chemical agents are impermeant to the cells, and the fluorescent probes are permeant to the cells. This allows the chemical agents to modify extracellular fluorescent probes while keeping a substantial amount of intracellular probes unmodified during the time frame of detection or measurement.

As used herein, a chemical agent is "impermeant" to a cell if the concentration of the chemical agent that enters the cell, if any, is no more than 1% of the concentration of the agent that resides outside the cell. Preferably, the concentration of the chemical agent inside the cell is no more than 0.5% of the concentration of the agent outside the cell. More preferably, the concentration of the agent inside the cell is no more than 0.25% of the concentration of the agent outside the cell. Highly preferably, the concentration of the agent in the cell is no more than 0.1% of the concentration of the agent outside the cell.

A fluorescent agent is "permeant" to a cell if the concentration of the fluorescent agent that enters the cell is at least 5% of the concentration of the fluorescent agent that stays outside the cell. Preferably, the concentration of the fluorescent agent in the labeled cell is at least 10% of the concentration of the agent outside the cell. More preferably, the concentration of the fluorescent agent in the labeled cell is at least 20% of the concentration of the agent outside the cell. Highly preferably, the concentration of the fluorescent agent in the cell is at least 30%, such as at least 40%, 50% or 60%, of the concentration of the agent outside the cell. The fluorescent agent can cross the intact cell membrane through either passive or active transportation.

Any type of fluorescent probe can be used in the present invention. Suitable fluorescent probes include, but are not limited to, nucleic acid probes, polypeptide probes, lipid and membrane probes, carbohydrate probes, intracellular radical probes, intracellular free-ion probes, pH probes, membrane potential probes, enzyme activity probes, cell viability probes, cell proliferation probes, and probes for cell enumeration. Examples of these fluorescent probes are described in the Handbook of Fluorescent Probes and Research Products ($9^{th}$ edition, Molecular Probes, Inc.), which is incorporated herein by reference in its entirety.

In one embodiment, the cell-permeant SYTO family of dyes (Molecular Probes) is used to label the cells of interest. SYTO dyes can passively diffuse through the membranes of most cells, including mammalian cells, yeast and bacteria. SYTO dyes bind to the DNA and RNA in the cells. The dyes have high molar absorptivity, and their quantum yields when bound to nucleic acids can be greater than 0.4. In a preferred embodiment, SYTO 62 red fluorescent nucleic acid stain is used in the present invention. SYTO 62 has the maximum excitation wavelength at 649 nm and the maximum emission wavelength at 680 nm.

Chemical agents that are used to reduce background fluorescence can chemically modify one or more functional groups in the fluorescent probes. Suitable chemical modifications include, but are not limited to, conversion, substitution, deletion, addition, oxidation and reduction. These modifications reduce or eliminate the fluorescence of the modified probes. Preferably, the chemical agents are impermeant to the cells. This allows the chemical agents to modify and quench extracellular fluorescent probes, but not intracellular ones. Because the extracellular fluorescent probes give rise to background fluorescence, chemical modification of these probes results in the reduction or elimination of background fluorescence.

Selection of suitable chemical agents depends on the chemical property of the fluorophore to be modified. For instance, if the fluorophore has an aromatic amine group, an oxidizing agent such as persulfate can be used to covert the group to an N oxide or nitro group, thereby eliminating the fluorescence of the fluorophore. For another instance, if the fluorophore contains a ring system with a carboxylic acid group, oxidative decarboxylation can be carried out to abolish the fluorophore's fluorescence. This can be done, for example, by using an oxidizing agent such as persulfate.

Persulfate is a potent oxidant which can produce different types of products. It can, for example, oxidize amines to nitrites, nitro groups, n oxides, and various hydroxylamines. It can also oxidize $C=C$ double bonds which are common in fluorescent compounds. In some instances, oxidation of $C=C$ bonds may lead to cleavage, giving rise to two ketones, or a ketone and a carboxylic acid depending on the initial structure, and thereby destroy or alter the fluorescence properties of the compounds.

Examples of other chemical agents suitable for the present invention include, but are not limited to, sodium, potassium, and other alkali salts of metabisulfite, thiosulfate, and hydrosulfite. These chemicals are capable of reducing $C=C$ to $CH_2$—$CH_2$, thereby changing the fluorescence properties of a variety fluorescent probes.

In one embodiment, the fluorescent probe is modified by adding a hydroxyl group on its ring system. This can be carried out using a reagent such as peracetic acid under mild or dilute conditions.

In another embodiment, a flow cytometer is used for detecting microbes labeled with fluorescent probes. The microbes can be yeast or bacteria. Suitable bacteria include gram negative bacteria, such as *E. coli*, or gram positive bacteria, such as *Bacillus subtilis*. The microbes can be first labeled with SYTO 62 which binds to the DNA and RNA inside the microbes. The sample containing the SYTO-labeled microbes is then treated with a reducing agent for about 1 to 15 minutes. Suitable reducing agents include sodium metabisulfite, sodium persulfate and sodium thiosulfate. Preferably, the concentration of the reducing agent in the sample ranges between 5 to 100 mM. The treated sample is subsequently loaded to the flow cytometer for detecting the SYTO-labeled microbes.

Preferably, the fluorescence emission from the sample, after subtracting the fluorescence emission from the SYTO-labeled cells, is reduced by at least 10% after the treatment with the reducing agent, as compared to before the treatment. More preferably, the fluorescence emission from the sample, after subtracting the fluorescence emission from the SYTO-labeled cells, is reduced by at least 20% after the treatment as compared to before the treatment. In certain cases, the fluorescence reduction can be as high as at least 50% or more, such as at least 60%, 70% or 80%.

Figure 1:
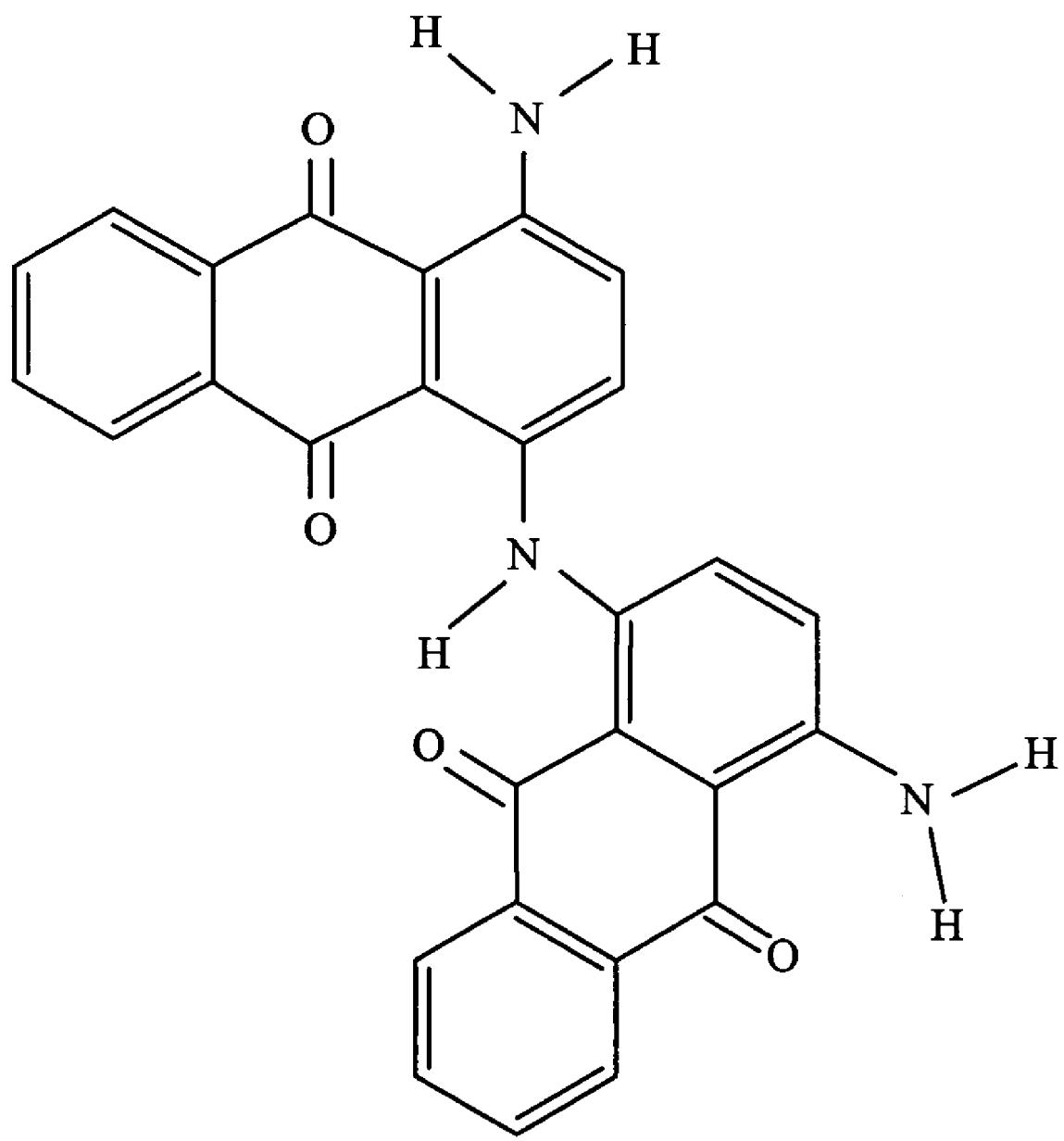
FIG. 1 depicts the chemical structure of Acid Black 48.

In accordance with another aspect of this invention, Acid Black 48 is used to reduce background fluorescence produced by fluorescent probes such as SYTO 62. FIG. 1 illustrates the chemical structure of Acid Black 48. Acid Black 48 has the maximum absorption wavelength at 663 nm. Its absorption profile overlaps the emission profile of SYTO 62.

Acid Black 48 can be used in the range from 1 µM to 100 nM with the preferred concentration of 22 µM. Acid Black 48 is not toxic to cells at 22 µM during an one-hour exposure. It is mildly toxic to *E. coli* but not toxic to *Bacillus subtilis* when used at 100 µM. Preferably, the cells are first labeled with SYTO 62 before Acid Black 48 is added to reduce background fluorescence.

In one embodiment, Acid-Black 48 is used to reduce background fluorescence in a flow cytometric measurement. The sample containing the microbes to be detected is first labeled with SYTO 62. Acid Black 48 is then added to quench extracellular SYTO 62. The sample is subsequently introduced into a flow cytometer to detect the labeled microbes.

EXAMPLE 1

Background Fluorescence Reduction in Cell-Free Solutions

A cell-free solution containing 10 mM phosphate (pH 7.2) and 100 nM Syto 62 (Molecular Probes, Inc.) was introduced into a flow cytometer. Fluorescence and side scatter signals were collected, and their respective intensities were plotted against the x- and y-axis, as shown in FIG. 2.

Figure 2:
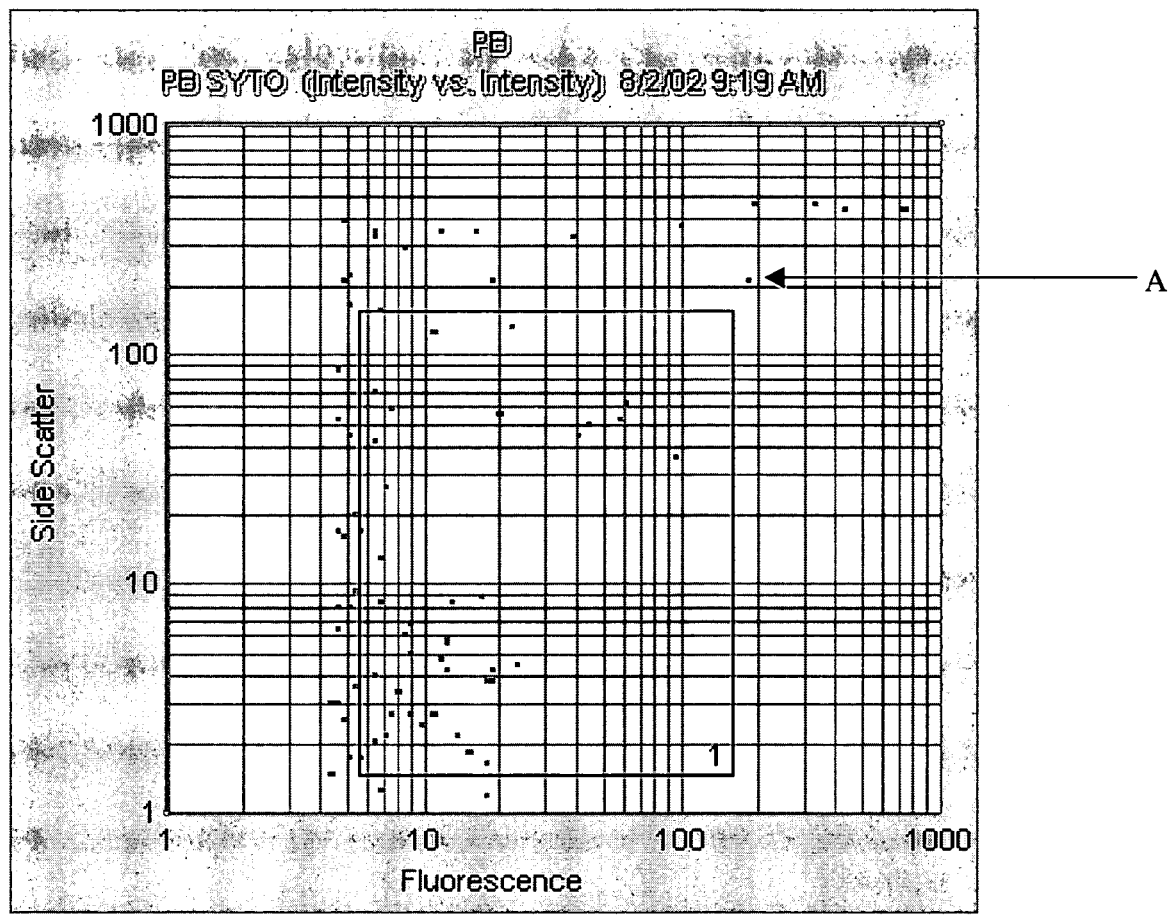
FIG. 2 shows a side scatter versus fluorescence plot of a cell-free solution.

Each spot in FIG. 2 corresponds to an individual count, meaning that the instrument was triggered by a fluorescent object to acquire data as the object traveled through the flow cytometer. The solution did not contain detectable cells. Therefore, the spots in FIG. 2 correspond to particles in the solution that were labeled with enough fluorescent dye (SYTO 62) to trigger the instrument. Each of these particles has its own size, shape and intensity of fluorescence. The location of the spot indicates both its fluorescence intensity (read from the x-axis) and its scattered light intensity (read from the y-axis). For example, the object labeled "A" in FIG. 2 corresponds to a fluorescent particle of unknown composition with a relative fluorescence intensity of just under 200 (see the logarithmic x-axis value) and a relative scattered light intensity of just over 200 (see the logarithmic y-axis value).

Figure 3:
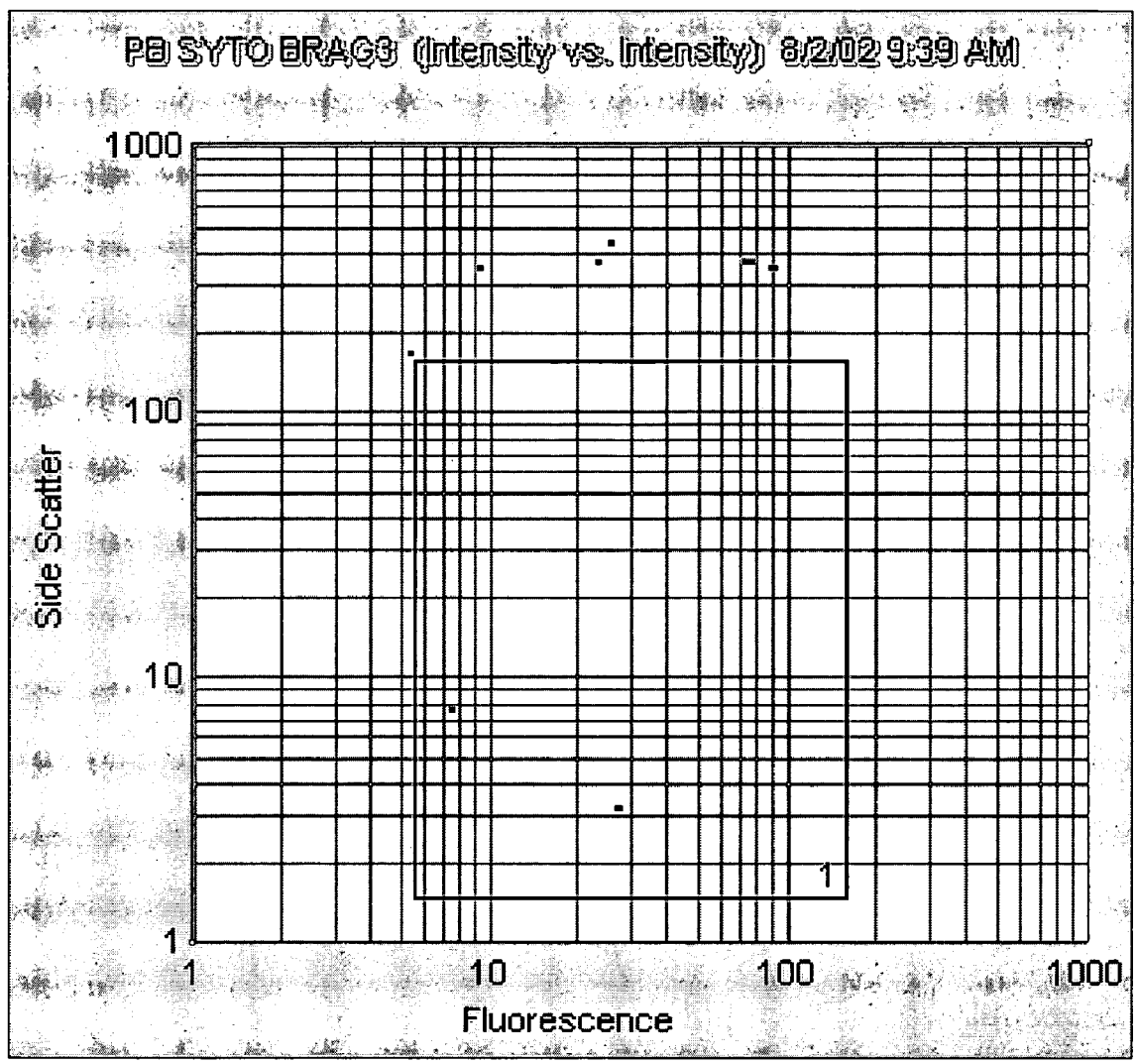
FIG. 3 illustrates a side scatter versus fluorescence plot of a cell-free solution containing Acid Black 48.

The software associated with the flow cytometer can define one or more regions of interest (ROI), such as box "1"

in FIGS. 2 and 3, and boxes "1" and "2" in FIGS. 4 and 5. The instrument can report the total "counts" that fall within a selected box.

The total counts in FIG. 2 and box 1 were 77 and 42, respectively. These counts represent the intensity of background fluorescence.

FIG. 3 shows the scatter versus fluorescence plot for a solution containing 10 mM phosphate buffer (pH 7.2), 100 nM Syto 62, and 22 µM Acid Black 48. Note the substantial decrease in background counts resulting from the addition of Acid Black. The total background counts in FIG. 3 and box 1 were 9 and 2, respectively.

EXAMPLE 2

Background Fluorescence Reduction in Solutions Containing Labeled Microbes

A solution containing 100 nM Syto 62 and an expected population of 14,400 cells/mL of *Enterococcus fecaelis* was introduced into a flow cytometer. FIG. 4 illustrates the scatter versus fluorescence plot of the solution. Two regions of interest in FIG. 4 were selected (box 1 and box 2). Most counts in box 1 correspond to signals produced by debris in the solution, such as mineral particulates. Most counts in box 2 (lower) correspond to signals produced by the cells in the solution. The total counts in boxes 1 and 2 were 902 and 2973, respectively. The total counts in FIG. 4 were 6396.

FIG. 5 shows the scatter versus fluorescence plot of the same solution as in FIG. 4, except that 22 µM Acid Black 48 was added. A significant reduction in background fluorescence was observed in FIG. 5, as compared to FIG. 4. The total counts in box 2 were 2684, while the total counts in box 1 was dramatically reduced to 160. The total counts in FIG. 5 was 3314, as compared to 6396 in FIG. 4.

The expected cell count of 14,400 cells/mL was determined from standard plate counts. The sample size used in FIGS. 4 and 5 was 0.25 mL, thus having expected cell counts of about 3,600.

It should be understood that the above-described embodiments and the following examples are given by way of illustration, not limitation. Various changes and modifications within the spirit and scope of the present invention will become apparent to those skilled in the art from the present description. Thus, it is noted that the scope of the invention is defined by the claim and their equivalents.

What is claimed:

1. A method for reducing background fluorescence from extracellular particulates in a solution, comprising the steps of:
   (i) labeling one or more cells in the solution with a fluorescent agent which is permeant to said one or more cells and capable of producing a fluorescence emission, the fluorescent agent also associating with one or more extracellular particulates present in the solution;
   (ii) contacting said solution and extracellular particulates with a chemical agent which is impermeant to said one or more cells; and
   (iii) introducing said solution into a flow cytometer and detecting said one or more cells,
   wherein the chemical agent chemically modifies the fluorescent agent associated with the extracellular particulates in said solution such that the fluorescence emission produced from said solution and extracellular particulates, after subtracting the fluorescence emission produced from said one or more labeled cells, is reduced by at least 10%.

2. A method for reducing background fluorescence from extracellular particulates in a solution, comprising the steps of:
   (i) labeling one or more cells in the solution with a fluorescent agent which is permeant to said one or more cells and capable of producing a fluorescence emission, the fluorescent agent also associating with one or more extracellular particulates present in the solution;
   (ii) contacting said solution and extracellular particulates with Acid Black 48; and
   (iii) introducing said solution into a flow cytometer and detecting said one or more cells,
   wherein the fluorescence emission produced from said solution and extracellular particulates, after subtracting the fluorescence emission produced from said one or more labeled cells, is reduced by at least 10% compared to before said contacting.

3. The method of claim 1, wherein the particulates comprise mineral particulates.

4. The method of claim 1, wherein the chemical agent comprises Acid Black 48.

5. The method of claim 1, wherein the fluorescent agent comprises a nucleic acid probe.

6. The method of claim 2, wherein the particulates comprise mineral particulates.

7. The method of claim 2, wherein the fluorescent agent comprises a nucleic acid probe.

8. A method for reducing false positive counts from extracellular particulates detected by a flow cytometer, comprising the steps of:
   labeling one or more cells in a solution with a fluorescent agent which is permeant to the one or more cells and capable of producing a fluorescence emission, the fluorescent agent also associating with one or more extracellular particulates present in the solution;
   contacting the solution with a chemical agent which is impermeant to the one or more cells; and
   introducing the solution into a flow cytometer and detecting the one or more cells,
   wherein the chemical agent quenches the fluorescent agent associated with extracellular particulates in the solution to reduce false positive counts detected by the flow cytometer.

9. The method of claim 8, wherein the particulates comprise mineral particulates.

10. The method of claim 8, wherein the chemical agent comprises Acid Black 48.

11. A method for reducing false positive counts from extracellular particulates detected by a flow cytometer, comprising the steps of:
    labeling one or more cells in a solution with a fluorescent agent comprising nucleic acid probe SYTO 62, the fluorescent agent also associating with one or more extracellular particulates present in the solution;
    contacting the solution with a chemical agent comprising Acid Black 48; and
    introducing the solution into a flow cytometer and detecting the one or more cells,
    wherein the chemical agent quenches fluorescent agent associated with extracellular particulates in the solution to reduce false positive counts detected by the flow cytometer.

* * * * *